(12) United States Patent
Ouyang et al.

(10) Patent No.: US 6,420,128 B1
(45) Date of Patent: Jul. 16, 2002

(54) TEST STRIPS FOR DETECTING THE PRESENCE OF A REDUCED COFACTOR IN A SAMPLE AND METHOD FOR USING THE SAME

(75) Inventors: Tianmei Ouyang, Fremont; Yeung Siu Yu, Pleasanton, both of CA (US)

(73) Assignee: LifeScan, Inc., Milpitas, CA (US)

( * ) Notice: Subject to any disclaimer, the term of this patent is extended or adjusted under 35 U.S.C. 154(b) by 34 days.

(21) Appl. No.: 09/659,938

(22) Filed: Sep. 12, 2000

(51) Int. Cl.$^7$ .............. C12Q 1/54; C12Q 1/26; C12Q 1/00
(52) U.S. Cl. .............. 435/14; 435/25; 435/4; 435/283.1; 435/975; 435/26
(58) Field of Search ............... 435/14, 25, 4, 435/283.1, 975, 26

(56) References Cited

U.S. PATENT DOCUMENTS 3,964,974 A * 6/1976 Banauch et al. ............... 435/14

FOREIGN PATENT DOCUMENTS

| EP | 0 908 453 A1 | 4/1997 |
|---|---|---|
| WO | WO 94/01544 | 7/1993 |
| WO | WO 94/01578 | 7/1993 |

* cited by examiner

*Primary Examiner*—Louise N. Leary
(74) *Attorney, Agent, or Firm*—Bret E. Field; Bozicevic, Field & Francis

(57) ABSTRACT

Test strips and methods for their use in the detection of an analyte in a sample are provided. The subject test strips are characterized by at least including a water soluble tetrazolium salt on a surface of a positively charged substrate. In many embodiments, the water soluble tetrazolium salt is present as part of an analyte oxidizing signal producing system, which system includes one or more of the following additional components: an analyte oxidizing enzyme, e.g., an analyte dehydrogenase or an analyte oxidase; an electron transfer agent; and an enzyme cofactor. Also provided are systems and kits incorporating the subject test strips. The subject test strips, systems and kits find use in the measurement of a wide variety of analytes in a sample, such as a physiological sample, e.g., blood or a fraction thereof.

25 Claims, 1 Drawing Sheet

TEST STRIPS FOR DETECTING THE PRESENCE OF A REDUCED COFACTOR IN A SAMPLE AND METHOD FOR USING THE SAME

FIELD OF THE INVENTION

The field of this invention is analyte measurement

BACKGROUND OF THE INVENTION

Analyte measurement in physiological fluids, e.g., blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include alcohol, formaldehyde, glucose, glutamic acid, glycerol, beta-hydroxybutyrate, L-lactate, leucine, malic acid, pyruvic acid, steroids, etc. In response to this growing importance of analyte measurement, a variety of analyte measurement protocols and devices for both clinical and home use have been developed. Many of the protocols and devices that have been developed to date employ a signal producing system to identify the presence of the analyte of interest in a physiological sample, such as blood.

While a variety of such signal producing systems have been developed to date for use in the measurement of a wide variety of different analytes, there continues to be a need for the further development of such systems.

Relevant Literature

Patent documents of interest include: EP 0 908 453 A1; WO 94/01578 and WO

SUMMARY OF THE INVENTION

Test strips and methods for their use in the detection of an analyte in a sample are provided. The subject test strips are characterized by at least including a water soluble tetrazolium salt on a surface of a positively charged substrate. In many embodiments, the water soluble tetrazolium salt is present as part of an analyte oxidizing signal producing system, which system includes one or more of the following additional components: an analyte oxidizing enzyme, e.g., an analyte dehydrogenase or an analyte oxidase; an electron transfer agent; and an enzyme cofactor. Also provided are systems and kits incorporating the subject test strips. The subject test strips, systems and kits find use in the measurement of a wide variety of analytes in a sample, such as a physiological sample, e.g., blood or a fraction thereof, or ISF (interstitial fluid).

DESCRIPTION OF THE SPECIFIC EMBODIMENTS

Figure 1:
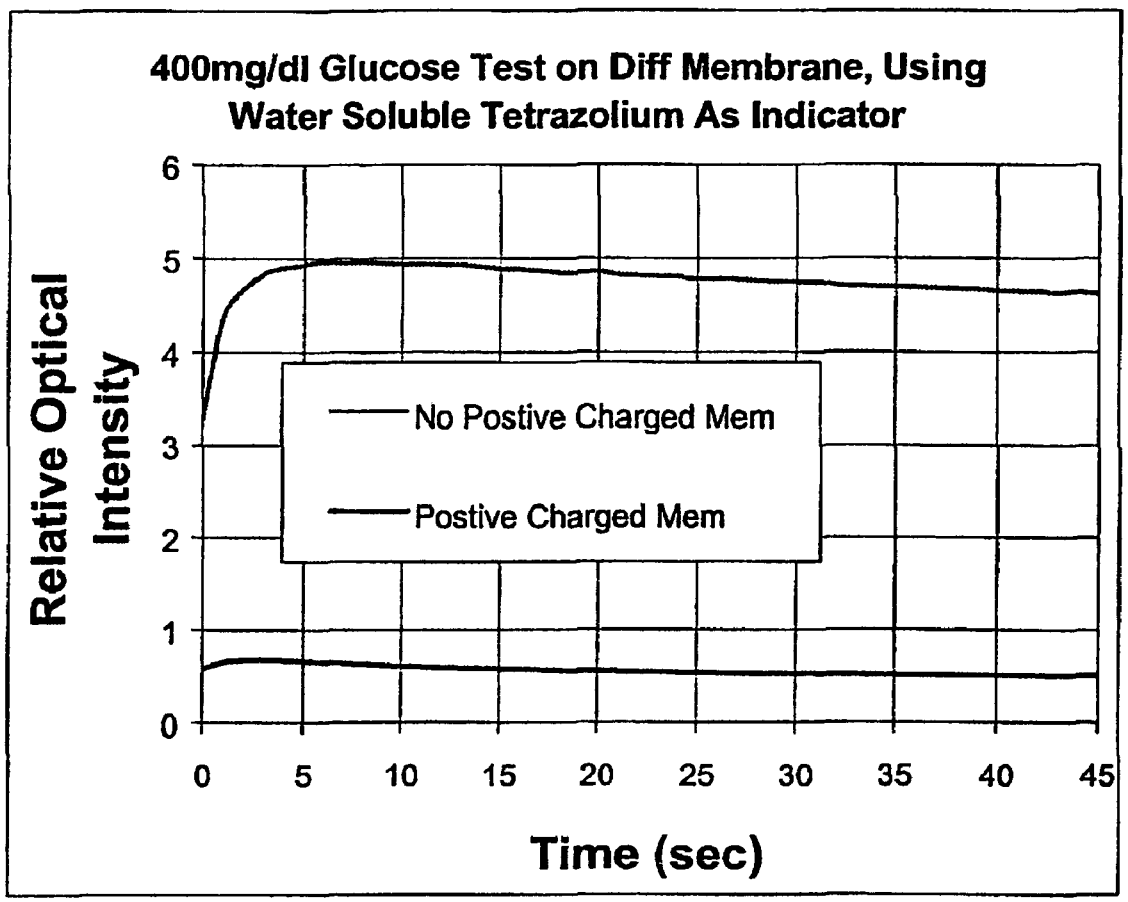
FIG. 1 provides the results of a 400 mg/dl Glucose Test conducted on positively charged and non-charged membranes, using water soluble tetrazolium as indicator according to the subject invention.

Test strips and methods for their use in the measurement of an analyte in a sample are provided. The subject test strips are characterized by at least including a water soluble tetrazolium salt on a surface of a positively charged substrate. In many embodiments, the water soluble tetrazolium salt is present as part of an analyte oxidizing signal producing system, which system includes one or more of the following additional components: an analyte oxidizing enzyme, e.g., an analyte dehydrogenase or an analyte oxidase; an electron transfer agent; and an enzyme cofactor. Also provided are systems and kits incorporating the subject test strips. The subject test strips, systems and kits find use in the detection of a wide variety of analytes in a sample, such as a physiological sample, e.g., blood or a fraction thereof, or ISF (interstitial fluid).

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

COMPOSITIONS

As summarized above, the subject invention provides compositions for use in detecting a wide variety of analytes in a sample. The compositions include a positively charged substrate and water soluble tetrazolium salt present on the surface of the substrate, typically as a member of an analyte oxidizing signal producing system. The subject compositions are typically present as dry compositions, such as are found in reagent test strips. In particular, the invention provides strips for assaying for a particular analyte in whole blood or a derivative fraction thereof, e.g., glucose, alcohol, glycated proteins, etc. In the broadest sense, the reagent test strips include a positively charged substrate and an analyte oxidizing signal producing system present on a surface of the substrate, which system includes a water soluble tetrazolium salt.

The above elements of the subject compositions are now further described in greater detail.

Positively Charged Substrate

A feature of the subject compositions is the presence of a positively charged substrate. By positively charged substrate is meant a substrate that displays one or more, usually a large plurality of, positive charges, e.g., as found on positively charged groups or moieties, on at least one of its surfaces. The substrate may be fabricated from a single material or may be a composite of two or more different materials, where these different materials may be blended, layered, or otherwise arranged to provide for the desired positively charged surface.

In addition, the positively charged substrate may be bibulous or non-bibulous. By bibulous is meant a material that exhibits preferential retention of one or more components as would occur, for example, in materials capable of absorbing or "imbibing" one or more components, as occurs in chromatographic separations. Examples of bibulous materials include, but are not limited to: untreated forms of paper, nitrocellulose and the like which result in chromatographic separation of components contained in liquids which are passed therethrough.

Alternatively, the positively charged substrate may be non-bibulous. Non-bibulous positively charged substrate include inert porous matrices which provide a support for the various members of the signal producing system, described infra, and have a positive charge. These matrices are generally configured to provide a location for application of a physiological sample, e.g., blood, and detection of the chromogenic product produced by the dye of the signal producing system. As such, the matrix is typically one that is permissive of aqueous fluid flow through it and provides sufficient void space for the chemical reactions of the signal producing system to take place. A number of different positively charged porous matrices have been developed for use in various analyte measurement assays, which matrices may differ in terms of materials, pore sizes, dimensions and the like, where representative matrices include those described in U.S. Pat. Nos: 55,932,431; 5,874,099; 5,871, 767; 5,869,077; 5,866,322; 5,834,001; 5,800,829; 5,800, 828; 5,798,113; 5,670,381; 5,663,054; 5,459,080; 5,459, 078; 5,441,894 and 5,212,061; the disclosures of which are herein incorporated by reference. The dimensions and porosity of the test strip may vary greatly, where the matrix may or may not have a porosity gradient, e.g., with larger pores near or at the sample application region and smaller pores at the detection region. Positively charged membranes can be prepared by using positively charged polymers, such as polyamide. Alternatively, such membranes can be prepared by various techniques, such as surface coating using cationic surfactants or polymers. The coating can be applied by dip coating, chemical treatment, photografting, plasma polymerization, etc. In yet other embodiments, the membrane can be prepared by means of blending one or more positively charged materials with the membrane forming polymer. Examples of positively charged polymers are polyamide, poly(vinyl pyridine), poly(vinyl imidazole), poly(allylamine), poly(vinyl benzyldimethyl ammonium chloride), polylysine and chitosan. Examples of cationic surfactants include those containing primary, secondary and quaternary amino groups. The material may or may not be functionalized to provide for covalent or noncovalent attachment of the various members of the signal producing system, described in greater detail infra.

In many embodiments, the matrix is configured as a membrane test pad and is affixed to a solid support, where the support may be a plastic (e.g., polystyrene, nylon or polyester) or metallic sheet or any other suitable material known in the art. Of interest in many embodiments are the test strip configurations disclosed in U.S. Pat. Nos. 5,972, 294; 5,968,836; 5,968,760; 5,902,731; 5,846,486; 5,843, 692; 5,843,691; 5,789,255; 5,780,304; 5,753,452; 5,753, 429; 5,736,103; 5,719,034; 5,714,123; 383,550; 381,591; 5,620,863; 5,605,837; 5,563,042; 5,526,120; 5,515,170; 367,109; 5,453,360; 5,426,032; 5,418,142; 5,306,623; 5,304,468; 5,179,005; 5,059,394; 5,049,487; 4,935,346; 4,900,666 and 4,734,360, the disclosures of which are herein incorporated by reference.

Signal Producing Systems

As summarized above, a feature of the subject compositions is that they include at least one water soluble tetrazolium salt, which component is typically present in conjunction with one or more members of an analyte oxidizing signal producing system. Specifically, a feature of the subject compositions is the presence of a water soluble tetrazolium salt that is capable of accepting a hydride to product a water soluble, colored formazan product. Water soluble tetrazolium salts of interest include those described in EP 0 908 453, the disclosure of which is herein incorporated by reference. One class of water soluble tetrazolium salts of interest include those described by formula 2 on page 2, lines 35 to 48 of EP 0 908 453. Another class of water soluble tetrazolium salts of interest include those described by formula 1 on page 3, lines 10–25 of EP 0 908 453.

Specific water soluble tetrazolium compounds or salts that are of particular interest include, but are not limited to: 2,2'-dibenzothiazolyl-5,5'-bis[4-di(2-sulfoethyl) carbamoylphenyl]-3,3'-(3,3'-dimethoxy- 4,4'-biphenylene) ditetrazolium, disodium salt (WST-5); 2-benzothiazolyl-3-(4-carboxy-2-methoxyphenyl)-5-[4-(2-sulfoethylcarbamoyl)phenyl]-2H-tetrazolium (WST-4) and the like. WST-5 is preferred in many embodiments because it readily dissolves in an aqueous medium, which is most compatible with biological samples. Furthermore, the resulting formazan compound exhibits strong spectral absorption at the purple-blue region, thus reducing the need for correcting the background signal from hemoglobin.

As mentioned above, the water soluble tetrazolium salt is typically present as a member of an analyte oxidizing signal producing system. By signal producing system is meant a collection of two or more compounds or molecules which are capable of acting in concert, when combined, to produce a detectable signal that is indicative of the presence of, and often amount of, a particular analyte in a given sample. The term signal producing system is used broadly to encompass both a mixture of all of the reagent constituents of the signal producing system as well as a system in which one or more of the reagent constituents are separated from the remainder of the reagent constituents, e.g., as is present in a kit.

As mentioned above, the signal producing system of the subject compositions and test strips is a analyte oxidizing signal producing system. The analyte oxidizing agent is generally an enzyme that is capable of removing a hydride from the analyte of interest to produce an oxidized form of the analyte. Analyte oxidizing enzymes of interest include analyte oxidases and analyte dehydrogenases. Analyte oxidases of interest include, but are not limited to: glucose oxidase (where the analyte is glucose); cholesterol oxidase (where the analyte is cholesterol); alcohol oxidase (where the analyte is alcohol); bilirubin oxidase (where the analyte is bilirubin); choline oxidase (where the analyte is choline); formaldehyde dehydrogenase (where the analyte is formaldehyde); glutamate oxidase (where the analyte is L-glutamic acid); glycerol oxidase (where the analyte is glycerol); galactose oxidase (where the analyte is galactose); L-ascorbate oxidase (where the analyte is ascorbic acid); lactate oxidase (where the analyte is lactic acid); leucine oxidase (where the analyte is leucine); malate oxidase (where the analyte is malic acid); pyruvate oxidase (where the analyte is pyruvic acid); urate oxidase (where the analyte is uric acid); and the like.

Analyte dehydrogenases of interest include, but are not limited to: alcohol dehydrogenase for alcohol; formaldehyde dehydrogenase for formaldehyde; glucose dehydrogenase for glucose; glucose-6-phosphate dehydrogenase for glucose-6-phosphate; glutamate dehydrogenase for glutamic acid; glycerol dehydrogenase for glycerol; beta-hydroxybutyrate dehydrogenase for beta-hydroxybutyrate; hydroxysteroid dehydrogenase for steroid; L-lactate dehydrogenase for L-lactate; leucine dehydrogenase for leucine; malate dehydrogenase for malic acid, and pyruvate dehydrogenase for pyruvic acid.

In many embodiments, the subject signal producing systems also include an enzyme cofactor that is capable of interacting with the oxidizing agent in a manner such that the analyte of interest is oxidized by the oxidizing agent, which agent concomitantly reduces the enzyme cofactor. Enzyme cofactors of interest include, but are not limited to: i.e., beta-nicotinamide adenine dinucleotide (beta-AND); beta-nicotinamide adenine dinucleotide phosphate (beta-NADP); thionicotinamide adenine dinucleotide; thionicotinamide adenine dinucleotide phosphate; nicotinamide 1, N6-ethenoadenine dinucleotide; nicotinamide 1, N6-ethenoadenine dinucleotide phosphate; and pyrroloquinoline quinone (PQQ). Enzyme cofactors of particular interest that may be included in the subject signal producing systems include: NADH or AND(P)H.

In addition to the analyte oxidizing agent, the subject signal producing systems typically include an electron transfer agent. By electron transfer agent is meant a compound or molecule that can transfer an electron, in the form of a hydride ion, from a reduced enzyme cofactor to the water soluble tetrazolium product. Electron transfer agents of interest include both low and high molecular weight electron transfer agents. In this specification, low molecular weight means a molecular weight that does not exceed about 2000 daltons, usually about 1000 daltons and in many embodiments about 500 daltons. High molecular weight means a molecular weight of at least about 5000 daltons and in many embodiments 10,000 or 20,000 daltons or higher. The molecular weight of the high molecular weight electron transfer agent often will not exceed about 100,000 daltons. In many embodiments, the low molecular weight electron transfer agent is a non-proteinaceous compound while the high molecular weight electron transfer agent is a proteinaceous compound. By proteinaceous is meant a polypeptide or polymeric mimetic thereof.

A variety of low molecular weight non-proteinaceous electron transfer agents are of interest. These agents include: flavins such as riboflavin (RBF), alloxazine (ALL) and lumichrome (LC); phenazines such as phenazine, phenazine methosulfate (PMS), phenazine ethosulfate, methoxyphenazine methosulfate and safranine; methyl-1, 4-naphthol (menadione), phenothiazines such as PT and its radical cation, PT+, thionin (TH), azure A (AA), azure B (AB), azure C (AC), methylene blue (MB), methylene green (MG) and toluidine blue 0 (TOL); phenoxazines such as phenoxazine (POA), basic blue 3 (BB3), and brilliant cresyl blue ALD (BCBA), benzo-a-phenazoxonium chloride (Medola's blue); Indophenols such as 2,6-dichlorophenol indophenol (DCIP); and Indamines such as Bindschedler's green and phenylene blue; and the like. Of particular interest in many embodiments are phenazine compounds, e.g. PMS, phenazine ethosulfate, methoxyphenazine methosulfate and safranine, where PMS is the low molecular weight, non-proteinaceous electron transfer agent in many embodiments.

In many embodiments, the high molecular weight proteinaceous electron transfer agent is an enzyme that is capable of oxidizing a reduced cofactor, e.g. AND(P)H, and concomitantly reducing the tetrazololium salt of the signal producing system. In many embodiments, this electron transfer enzyme is a diaphorase, such as lipoic dehydrogenase, ferredoxin-NADP reductase, lipoamide dehydrogenase, NADPH dehydrogenase, etc. A variety of diaphorases are available and may be employed, where representative commercially available diaphorases that may be present in the subject signal producing systems include bacillus diaphorase, clostridium diaphorase, vibrio diaphorase, porcine diaphorase, and the like.

The signal producing systems described above are generally present in the subject compositions as reagent compositions. In many embodiments the reagent compositions are dry compositions. At a minimum, the subject reagent compositions are ones that include the water soluble tetrazolium salt. In many embodiments, however, the reagent compositions further include an enzyme cofactor, an analyte oxidizing enzyme and an electron transfer agent, where these components are described above.

REAGENT TEST STRIPS

Of particular interest in many embodiments of the subject invention are reagent test strips that include the above described compositions and are intended for use in measuring the presence or concentration of an analyte in a sample. In particular, the invention provides dry strips for assaying for a particular analyte in whole blood, e.g., beta-hydroxybutyrate, glucose, etc. In the broadest sense, the reagent test strip includes a positively charged solid support and a dry reagent composition present thereon, where the dry reagent composition is made up of all of the reagent compounds necessary to produce a detectable signal in the presence of the analyte of interest. In most embodiments of the subject invention, the dry reagent composition present on the subject test strip is one that includes the following members: an analyte oxidizing enzyme, an enzyme cofactor, an electron transfer agent and a water soluble tetrazolium salt, where each of these constituent members are described in greater detail above.

In many embodiments, the subject test strips include a membrane test pad that is affixed to a solid support. The support may be a plastic—e.g., polystyrene, nylon, or polyester—or metallic sheet or any other suitable material known in the art. Associated with the test pad, e.g., coated onto the test pad, incorporated into the test pad, etc., is the reagent composition. The strip may also be configured in more complex arrangements, e.g., where the test pad is present between the support and a surface layer, where one or more reagents employed in sample processing may be present on the surface layer. In addition, flow paths or channels may be present on the test strip, as is known in the art. Of interest in many embodiments are the test strip configurations disclosed in U.S. Pat. No. 5,902,731, the disclosure of which is herein incorporated by reference.

The subject test strips may be fabricated employing any convenient protocol. One convenient protocol is to contact at least the test pad portion of the strip with an aqueous composition that includes all of the members of the reagent composition that is to be associated with the test pad in the final reagent test strip. Conveniently, the test pad may be immersed in the aqueous composition, maintained therein for a sufficient period of time and then dried, whereby the test pad of the reagent test strip which has associated therewith the reagent composition is produced. As stated above, the aqueous composition will include the various members of the reagent composition to be associated with the test pad of the reagent test strip, where the various members are present in amounts sufficient to provide for the desired amounts in the reagent composition that is produced on the test pad. As such, where the electron transfer agent is non-proteinaceous, the concentration of electron transfer agent present in this aqueous composition typically ranges from about 10 to 50,000, usually from about 50 to 10,000 and more usually from about 100 to 5,000 $\mu$M. In other embodiment where the electron transfer agent is proteinaceous, the concentration of the electron transfer agent present in the aqueous composition typically ranges from about 10 to 10,000, usually from about 50 to 5,000 and more usually from about 100 to 3,000 U/ml. The concentration of tetrazolium salt present in the aqueous composition ranges from about 3 mM to 36 mM, usually from about 6 mM to 24 mM. When present, the enzyme cofactor ranges in concentration from about 1.5 mM to 28 mM, usually from about 3.5 mM to 14 mM. Similarly, the analyte oxidizing agent enzyme ranges in concentration from about 100 U to 2000 U, and usually from about 200 U to 1000 U when present. See the experimental section, infra, for a more detailed description of a representative method for preparing the subject reagent test strips.

METHODS OF ANALYTE MEASUREMENT

The above described signal producing systems, reagent compositions and test strips find use in methods of detecting the presence of, and often the amount of, i.e., the concentration of, an analyte in a sample. A variety of different analytes may be detected using the subject methods, where representative analytes include those described above, e.g., alcohol, formaldehyde, glucose, glutamic acid, glycerol, beta-hydroxybutyrate, L-lactate, leucine, malic acid, pyruvic acid, steroids, etc. While in principle, the subject methods may be used to determine the presence, and often concentration, of an analyte in a variety of different physiological samples, such as urine, tears, saliva, and the like, they are particularly suited for use in determining the concentration of an analyte in blood or blood fractions, e.g., blood derived samples, and more particularly in whole blood, ISF (interstitial fluid).

In the subject methods, the sample and the signal producing system are combined into a reaction mixture, the reaction is allowed to proceed for a sufficient period to time to generate a signal indicative of the presence of (and often amount of) analyte in the sample, and the resultant signal is detected and related to the presence of (and often amount of) analyte in the sample. The above steps take place on a reagent test strip as described supra.

A feature of the subject methods is that the detectable signal is made up of a non-washable spot that forms on the surface of the substrate of the strip. The non-washable spot is made up of water soluble formazan product which is tightly bound to the substrate surface such that it cannot be readily removed from the surface under standard washing conditions. By standard washing conditions is meant the conditions experienced by substrate surface in analyte detection assays where unbound component has to be removed from the surface. An example of standard washing conditions are those employed by those of skill in the art in array based nucleic acid hybridization assays, where non-hybridized nucleic acids are removed from the surface of an array following a hybridization step. Such conditions are well known to those of skill in the art. As such, a feature of the subject methods is the production of a non-washable spot on the surface of the positively charged substrate, where the non-washable spot is made up of the water soluble formazan product.

In practicing the subject methods, the first step is to apply a quantity of the physiological sample to the test strip, where the test strip is described supra. The amount of physiological sample, e.g. blood, that is applied to the test strip may vary, but generally ranges from about 2 $\mu$L to 40 $\mu$L, usually from about 5 $\mu$L to 20 $\mu$L. Because of the nature of the subject test strip, the blood sample size that is applied to the test strip may be relatively small, ranging in size from about 2 $\mu$L to 40 $\mu$L, usually from about 5 $\mu$L to 20 $\mu$L. Where blood is the physiological sample, blood samples of a variety of different hematocrits may be assayed with the subject methods, where the hematocrit may range from about 20% to 65%, usually from about 25% to 60%.

Following application of the sample to the test strip, the sample is allowed to react with the members of the signal producing system to produce a detectable product, i.e., the non-washable spot, that is present in an amount proportional to the initial amount of the analyte of interest present in the sample. The amount of detectable product, i.e., signal produced by the signal producing system in the form of the non-washable spot, is then determined and related to the amount of analyte in the initial sample. In certain embodiments, automated instruments that perform the above mentioned detection and relation steps are employed. The above described reaction, detection and relating steps, as well as instruments for performing the same, are further described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,902,731; 5,968,836 and 5,972,294; the disclosures of which are herein incorporated by reference. In the relation step, the derived analyte concentration takes into account the constant contribution of competing reactions to the observed signal, e.g., by calibrating the instrument accordingly.

KITS

Also provided by the subject invention are kits for use in practicing the subject methods. The kits of the subject invention at least include a signal producing system as described above, where the signal producing system components may be combined into a single reagent composition or separated, e.g., present in separate containers. In certain embodiments, the signal producing system will be present in the kits in the form of a reagent test strip, as described supra. The subject kits may further include a means for obtaining a physiological sample. For example, where the physiological sample is blood, the subject kits may further include a means for obtaining a blood sample, such as a lance for sticking a finger, a lance actuation means, and the like. In addition, the subject kits may include a control solution or standard, e.g. an analyte control solution that contains a standardized concentration of analyte. In certain embodiments, the kits also include an automated instrument, as described above, for detecting the amount of product produced on the strip. following sample application and relating the detected product to the amount of analyte in the sample. Finally, the kits include instructions for using the subject kit components in the determination of an analyte concentration in a physiological sample. These instructions may be present on one or more of the packaging, a label insert, containers present in the kits, and the like.

The following examples are offered by way of illustration and not by way of limitation.

EXPERIMENTAL

EXAMPLE 1

A 0.8 $\mu$m nylon membrane obtained from Pall Corporation (East Hills, N.Y.) was dipped into the reagent of Table 1, until saturated. The excess reagent was scraped off gently with a glass rod. The resulting membrane was hung to dry in a 56° C. oven for 10 minutes. Porex (0.6 mm thick) was soaked in the nitrite solution of Table 2 and then hung to dry in a 1000° C. oven for ten hours. Finally, the membrane was laminated between a polyester stock (0.4 mm Melenexg® polyester from ICI America, Wilmington, Del.) and the nitrite-impregnated Porex.

EXAMPLE 2

The procedure of Example 1 was repeated, except that the first dip was the reagent of Table 3, and there was no second dip, since the Porex was not needed.

TABLE 1

Reagent for a Glucose Test Pad

| Components | Quantity |
| --- | --- |
| Water | 100 ml |
| (2-[-Morpholino]ethanesulfonic acid) sodium salt MES (MW 217.2, Sigma, St. Louis, MO, USA) Adjust pH to 5–7 by adding 6 M HCl) | 2.2 gm |
| Tetonic 1307 (BASF Corporation, Mount Olive, New Jersey, USA) | 1–3 gm |
| PSSA, Polystyrenesulfonic acid, sodium salt (MW 70,000, Polysciences, Inc., Warrington, PA, USA) | 2–4 gm |
| Crotein (Croda Inc., Parsippany, NJ, USA) | 2–4 gm |
| Mannitol (MW 182, Sigma, St. Louis, MO, USA) | 1–10 gm |
| Phenazine Methosulfate (PMS, MW 306.34, Sigma, St. Louis, MO, USA | 30–300 mg |
| WST-5 (MW 1331.37, Dojindo Laboratory, Japan) | 0.8–4 gm |
| Glucose Oxidase (GO, TOYOBO) | 100–1000 KU |

TABLE 2

Nitrite Reagent

| Components | Quantity |
| --- | --- |
| 10 mM Phosphate Buffer Saline, pH 7.4, (P-3813, Sigma, St. Louis, MO, USA) | 70 ml |
| Ethanol | 30 ml |
| Sodium Nitrite (MW69, Aldrich Chemicals, Milwaukee, WI, USA) | 5 gm |
| Polyvinylpyrrodine (MW 40,000, Sigma, St. Louis, MO, USA) | 200 mg |

TABLE 3

Reagent for a Glucose Test Pad

| Components | Quantity |
| --- | --- |
| Water | 100 ml |
| (2-[-Morpholino]ethanesulfonic acid) sodium salt MES (MW 217.2, Sigma, St. Louis, MO, USA) | 2.2 gm |
| Poly(methyl vinyl ether-alt-maleic anhydride)* 6% Adjust pH to 5.5–7 by adding 50% NaOH | 20 mL |
| Triton X-305 (BASF Corporation, Moun Olive, New Jersey, USA) | 0.5–2 gm |
| Mannitol (MW 182, Sigma, St. Louis, MO, USA) | 1–10 gm |
| Sodium Nitrite (MW69, Aldrich Chemicals, Milwaukee, WI, USA | 1–5 gm |
| WST-5 (MW 1331.37, Dojindo Laboratory, Japan) | 0.8–4 gm |
| Magnesium Chloride (MW 203, Sigma, St. Louis, MO, USA) | 3–5 gm |
| Phenazine Ethosulfate (PES, MW 334.4, Sigma, St. Louis, MO, USA) | 100–1000 mg |
| Glucose Oxidase (GO, TOYOBO) | 100–1000 KU |

*Poly(methylvinylether-alt-maleic anhydride), MW 1,080,000, Cat# 41632-0, Aldrich Chemicals, Milwaukee, WI, USA) Weigh out Poly (methylvinylether-alt-maleic anhydride) 6% in water (w/v), and heat the suspension to 95 C. for 45 min. The resulting solution is ready to use upon cooling to room temperature.

Various glucose standards were tested on the non-charged and positively charged membranes. The signals were linear from 50 to 450 mg/dl glucose levels in blood. FIG. 1 shows the same dip was coated on different membrane. One is positive charged nylon membrane, one is no positive charged polysulfone membrane. The coated membrane was tested by 400 mg/dl glucose.

Using the following protocol, 10 μL of aqueous samples comprising 400 mg/dL glucose were tested on strips as described above, where the membrane of the strips varied in terms of the positively charged nylon membrane and (no positive charged)(non-charged)polysulfone membrane on the strip. A 10 μl aqueous sample was applied onto a freshly prepared test strip. The strip was inserted into a reflectometer and data acquisition was commenced. The relectance of the reading strip was monitored at 615 nm at one-second intervals for forty five seconds. Next, the data were uploaded from the reflectometer's memory buffer to a personal computer via a modified serial cable. The reaction profile was plotted by K/S versus seconds. (K/S is a measure of reflectance, discussed and defined in U.S. Pat. No. 4,935,346, col. 14, the disclosure of which is herein incorporated by reference.)

It is evident from the above results and discussion that the subject invention provides for improvement over previous reagent test strip formats. By using a water soluble tetrazolium salt in combination with a positively charged substrate, the subject invention is the beneficiary of all of the positive attributes of tetrazolium compounds and is able to produce a non-washable reporter signal from the resultant water soluble formazan product. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A composition of matter comprising:
    a non-bibulous positively charged substrate; and at least one water soluble tetrazolium salt on at least one surface of said positively charged substrate.

2. The composition according to claim 1, wherein said water soluble tetrazolium salt is part of an analyte oxidizing signal producing system.

3. The composition according to claim 2, wherein said analyte oxidizing signal producing system comprises an analyte oxidase.

4. The composition according to claim 2, wherein said analyte oxidizing signal producing system comprises an analyte dehydrogenase.

5. The composition according to claim 2, wherein said analyte oxidizing signal producing system further comprises an electron transfer agent.

6. The composition according to claim 2, wherein said analyte oxidizing signal producing system further comprises an enzyme cofactor.

7. The composition according to claim 2, wherein said analyte oxidizing signal producing system is present as a reagent composition.

8. A reagent test strip comprising:
    a positively charged substrate; and
    an analyte oxidizing signal producing system present on said positively charged substrate, wherein said analyte oxidizing signal producing system includes a water soluble tetrazolium salt.

9. The test strip according to claim 8, wherein said positively charged substrate is bibulous.

10. The test strip according to claim 8, wherein said positively charged substrate is non-bibulous.

11. The test strip according to claim 8, wherein said water soluble tetrazolium salt accepts a hydride to produce a water soluble formazan product.

12. The test strip according to claim 8, wherein said analyte oxidizing signal producing system comprises an analyte oxidase.

13. The test strip according to claim 12, wherein said analyte oxidizing signal producing system further comprises an electron transfer agent.

14. The test strip according to claim 12, wherein said analyte oxidizing signal producing system further comprises an enzyme cofactor.

15. The test strip according to claim 8, wherein said analyte oxidizing signal producing system is a glucose oxidizing signal producing system.

16. An analyte detection or measurement system comprising:
    (a) a reagent test strip comprising:
        (i) a positively charged substrate; and
        (ii) an analyte oxidizing signal producing system present on said substrate, wherein said signal producing system includes a water soluble tetrazolium salt capable of accepting a hydride to produce a water soluble formazan; and
    (b) an automated instrument.

17. A method for detecting the presence or determining the concentration of an analyte in a sample, said method comprising:
    (a) applying said physiological sample to a reagent test strip comprising:
        (i) a positively charged substrate; and
        (ii) an analyte oxidizing signal producing system present on said substrate, wherein said signal producing system includes a water soluble tetrazolium salt capable of producing a water soluble formazan product, whereby a non-washable spot comprising said formazan product is produced on said substrate;
    (b) detecting said non-washable spot; and
    (c) relating said detected non-washable spot to the presence or concentration of said analyte in said physiological sample.

18. The method according to claim 17, wherein said signal producing system further comprises an analyte oxidase.

19. The method according to claim 18, wherein said signal producing system further comprises at least one of an electron transfer agent.

20. The method according to claim 17, wherein said sample is whole blood or a derivative thereof.

21. The method according to claim 17, wherein said detecting and relating steps are carried out by an automated instrument.

22. A kit for use in determining the concentration of an analyte in a physiological sample, said kit comprising:
    (a) a reagent test strip comprising:
        (i) a positively charged substrate; and
        (ii) an analyte oxidizing signal producing system present on said substrate, wherein said signal producing system includes a water soluble tetrazolium salt capable of producing a water soluble formazan product; and
    (b) at least one of:
        (i) a means for obtaining said physiological sample and
        (ii) an analyte standard.

23. The kit according to claim 22, wherein said means for obtaining said physiological sample is a lance.

24. The kit according to claim 22, wherein said analyte standard comprises a standardized concentration of a known reagent.

25. The kit according to claim 22, wherein said kit comprises a means for obtaining said physiological sample and an analyte standard.

\* \* \* \* \*